(12) United States Patent
Davis et al.

(10) Patent No.: US 6,982,794 B1
(45) Date of Patent: Jan. 3, 2006

(54) DIRECTIONAL REFLECTOMETER

(75) Inventors: Keith J. Davis, Issaquah, WA (US); Diane C. Rawlings, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 842 days.

(21) Appl. No.: 08/871,305

(22) Filed: Jun. 9, 1997

Related U.S. Application Data

(63) Continuation-in-part of application No. 08/484,576, filed on Jun. 7, 1995, now Pat. No. 5,637,873.

(51) Int. Cl.
*G01N 21/47* (2006.01)
*G01J 5/02* (2006.01)

(52) U.S. Cl. .................... 356/446; 356/51; 250/339.11; 250/341.8

(58) Field of Classification Search ......... 356/445–448, 356/51; 250/341.8, 372, 239.11, 352; 359/857–859, 359/864, 861
See application file for complete search history.

(56) References Cited

U.S. PATENT DOCUMENTS

| | | | | |
|---|---|---|---|---|
| 4,030,837 A | | 6/1977 | Kojima et al. ............... | 356/445 |
| 4,277,177 A | | 7/1981 | Larsen et al. ............... | 356/446 |
| 4,360,275 A | * | 11/1982 | Louderback ................ | 356/446 |
| 4,565,450 A | * | 1/1986 | Wirz et al. ................. | 356/402 |
| 4,601,576 A | * | 7/1986 | Galbraith ................... | 356/237 |
| 4,661,706 A | | 4/1987 | Messerschmidt et al. ... | 356/446 |
| 4,761,676 A | | 8/1988 | Wiles et al. ................ | 356/446 |
| 4,815,858 A | | 3/1989 | Snail .......................... | 356/446 |
| 4,902,131 A | * | 2/1990 | Yamazaki et al. .......... | 356/336 |
| 4,961,646 A | | 10/1990 | Schrammli et al. ......... | 356/448 |
| RE33,424 E | * | 11/1990 | Noguchi et al. ............ | 356/446 |
| 4,988,205 A | | 1/1991 | Snail .......................... | 356/446 |
| 5,078,496 A | | 1/1992 | Parket et al. ............... | 356/446 |
| 5,153,445 A | | 10/1992 | Stapleton ................... | 356/445 |

(Continued)

OTHER PUBLICATIONS

"New Device Measures Degradation of Sensor Windows Quickly, Accurately," AvWeek & Space Tech., May 13, 1991.
"Light Scatter: A New Light on Quality," TMA Technical Bulletin, vol. 1, No. 2, Sep. 15, 1991.
Kaplan, "How Clean is Clean?" Photonics Spectra, Jun., 1993.
"TMA µScan Surface Roughness and Scatter Measurement Instrumentation" [µScan Scatterometer], TMA Technologies, Inc., Jan. 30, 1992, [offered for sale to Boeing, Jun. 1, 1993].
"Laboratory Portable SpectroReflectometer Model LPSR–200–IR" AZ Technology, Inc. (no date).
"TEMP 2000 Portable Emissometer," AZ Technology, Inc. (no date).

*Primary Examiner*—Hoa Q. Pham
(74) *Attorney, Agent, or Firm*—John C. Hammar

(57) ABSTRACT

The present invention is a directional reflectometer that measures, for example, the optical bidirectional reflectance distribution function [BRDF] of a surface in situ on a finished article, e.g. a vehicle, to provide information on its surface reflectivity and emissivity. The light wavelength may be IR, near-IR, visible, UV, or longer wavelengths. Light, preferably focused to a small spot on the surface, is projected onto the surface at an angle adjustable in azimuth and elevation. A wide angle mirror, lens system, or both transfers light scattered from the surface onto an imaging sensor, preserving scattering angle information and thereby permitting the BRDFs for a given incidence angle and all scattering angles to be measured simultaneously. A computer reads the sensor outputs and analyzes the quality of the surface in a factory or field environment.

10 Claims, 5 Drawing Sheets

U.S. PATENT DOCUMENTS

| | | | |
|---|---|---|---|
| 5,229,835 A | 7/1993 | Reinsch | 356/446 |
| 5,293,211 A | 3/1994 | Bernard et al. | 356/400 |
| 5,337,144 A * | 8/1994 | Strul et al. | 356/357 |
| 5,376,793 A | 12/1994 | Lesniak | 250/330 |
| 5,416,594 A * | 5/1995 | Gross et al. | 356/237 |
| 5,465,145 A * | 11/1995 | Nakashige et al. | 356/237 |
| 5,605,838 A | 2/1997 | Backhaus et al. | 356/445 |
| 5,659,397 A * | 8/1997 | Miller et al. | 356/445 |

* cited by examiner

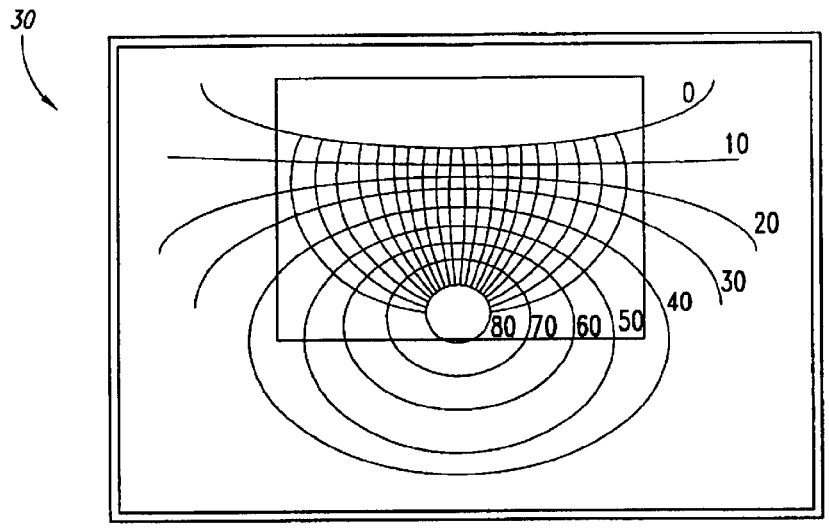
Fig. 6
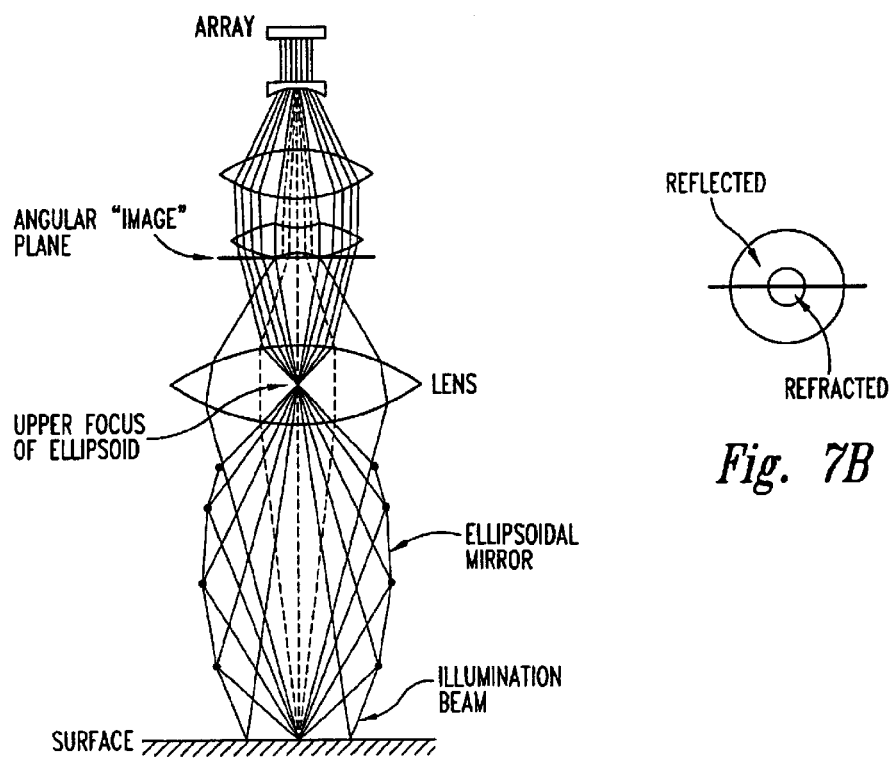
Fig. 7B
Fig. 7A

DIRECTIONAL REFLECTOMETER

REFERENCE TO RELATED APPLICATIONS

The present application is a continuation-in-part application based upon U.S. patent application Ser. No. 08/484,576, filed Jun. 7, 1995, now U.S. Pat. No. 5,637,873, issued Jun. 10, 1997, which we incorporate by reference.

STATEMENT REGARDING FEDERALLY SPONSORED RESEARCH OR DEVELOPMENT

This invention was made with Government support under Contract F3361595-C-5237 awarded by the Air Force. The Government has certain rights in this invention.

TECHNICAL FIELD

The present invention is an apparatus for laboratory or field measurement of the optical, UV, visible, or IR bidirectional reflectance from a surface. To determine the quality of a surface, the apparatus of the present invention measures full-hemisphere, nonintegrated directional reflectance of applied coatings.

BACKGROUND ART

It is difficult to measure accurately the emissivity or reflectivity of a surface, especially at low grazing angles. The need for reliable measurements is increasing, especially for military vehicles where these physical characteristics (and their control) are significant features for survival. Modern optical (infrared {IR} and visible) seekers detect these "signatures." Today, measurements of the bidirectional reflectance for an entire vehicle are difficult, expensive, and require a carefully controlled or measured environment.

The present invention addresses a need to measure that IR directional emissivity and reflectivity of surfaces and coatings. The emissivity and bidirectional reflectivity play a major role in determining an airframe's total IR signature. Coatings are often designed to produce particular emissivity/reflectivity characteristics. While techniques exist to measure these properties for small samples in the laboratory, none of these methods are suitable for measuring the properties of the coatings once they are applied to a large airframe.

In U.S. Pat. No. 5,505,543, Rawlings, et al. we described a laboratory emissometer for measuring the emissivity of sample coatings. This device is useful only for small samples and is not suitable for measuring the signature of a vehicle surface. It is, nevertheless, a useful tool for designing coatings. The emissometer operates by measuring the radiation emanating from the surface because of its temperature. This device is capable of measuring normal to grazing angle (0°–80° off normal) emittance spectrally and as a function of temperature between −65° F. and 400° F.

Surface Optics markets a portable measurement device that operates in the IR. ELDIM's EZContrast® measurement devices uses a CONOSCOPIC approach to obtain high speed measurement of the luminance of liquid crystal displays (LCDs) in the visible at zenith angles of 0–80° and angles of azimuth between 0–360°. ELDIM uses a Fourier lens and a relay lens to focus an image on a cooled CCD sensor to produce a viewing angle map.

Modern aircraft have specifications and requirements for emissivity and reflectivity (based on the IR signature goals) that present new issues relative to the inspection techniques and tools required for manufacturing and maintenance. In particular, the IR signature is affected by the exterior coating reflectance and emittance. The performance of the coating can be sensitive to variations in the coating materials or application processes and to environmental exposure. To assure that an aircraft meets IR specifications, IR coating performance must be tested as applied on the vehicle surface. Such measurements must be repeated on a regular maintenance schedule and after repairs to assure continuing signature performance. These measurements must be nondestructive, rapid, and require minimal skill level and training. Measurement devices should be easily portable (hand-held if possible), affordable, rugged, and require little support (standard power, detect at room temperature).

NDE (nondestructive evaluation) measurements must provide sufficient information to assess whether the surface meets coating and vehicle specifications. It is important that the information be of sufficient content and quality, and only useful information. In addition, the instrument should collect and process the data and provide pass/fail indication to the operator.

SUMMARY OF THE INVENTION

Our directional reflectometer is a compact system for measuring emissivity/reflectivity of coatings applied to laboratory coupons or, especially, to large objects not amenable to testing in the laboratory. It is particularly useful to measure IR properties of vehicles at maintenance depots or in the field. Its intended role is for quality assurance during manufacturing and in-field service to verify that coatings are performing properly. In the laboratory settings, the reflectometer provides a rapid and intuitive means for understanding the directionality of surface reflectance. We generally use reflective or refractive optics to form an "image" of the angular distribution of light reflecting as scattered light from the surface of interest. One embodiment allows virtually all of the light over a broad or narrow spectral band leaving a surface to be collected onto a single imaging array or possibly a non-imaging detector.

The reflectometer can be a small, traveling, broadband IR (3–$\mu$m) device or a UV, visible, and near IR (0.3–3 $\mu$m) device. It is attached to a portable computer including a microprocessor and a display. (FIG. 1) The computer analyzes the data collected at the imaging array and presents it in several formats, most notably a "pass-fail" based on whether the reflectance falls within a predetermined range. The reflectance criteria are flexible and can be based on quantities such as the bidirectional reflectance distribution function (BRDF), the total integrated hemispherical reflectance, the diffuse reflectance, the specular reflectance, or the specular lobe width. Reflection is measured at incident angles between normal and grazing (up to 88° from normal), and at reflected angles extending to 90° from normal. An angle-space "image" is formed of the scattered radiation, providing full directional reflectance information at a glance. The rapid response allows data to be collected continuously as the device is moved across a surface. The angle-space "image" contains enough information to assess both standard and special surfaces or coatings and can be integrated to determine total hemispherical reflectance. Portable computer-based analysis permits determination of pass-fail responses rapidly.

The cold aperture, gimbal mirror, and secondary mirror that we used in the reflectometer described in U.S. Pat. No. 5,637,873 are eliminated in our preferred design. The present design is simple and compact with reduced part count. Performance is unaffected. The cost of manufacture, assembly, and use are reduced because expensive components are eliminated. The resulting reflectometer is more robust, reliable, and durable.

BRIEF DESCRIPTION OF THE DRAWINGS

FIG. 6 is a graph showing mapping of angle space onto a 2-D plane.

FIG. 7A is an alternate embodiment using an ellipsoid reflector and a series of lenses.

FIG. 7B is a view along the angular "image" plane of FIG. 7A.

DETAILED DESCRIPTION OF A PREFERRED EMBODIMENT

Figure 1:
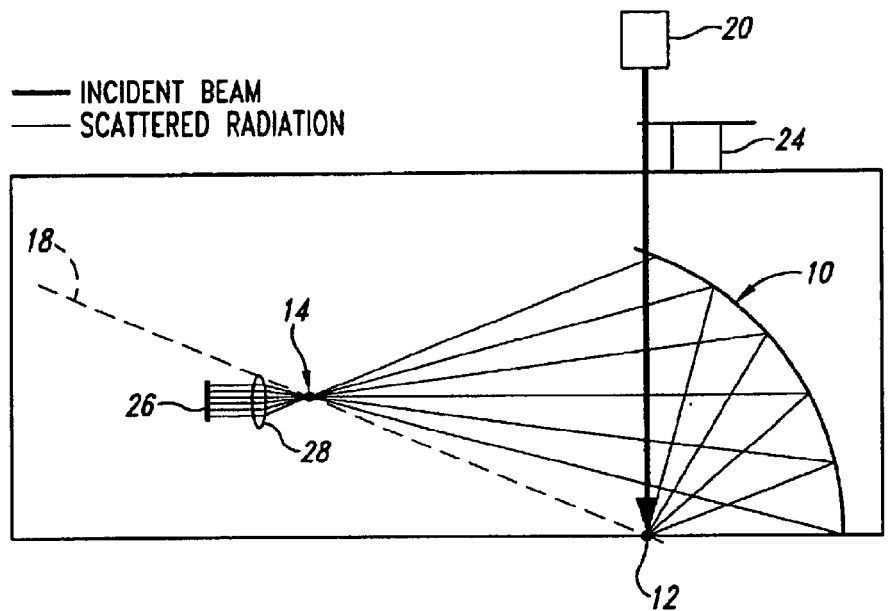
FIG. 1 illustrates in elevation a preferred reflectometer.

The directional reflectometer of the present invention in one embodiment measures the optical bidirectional reflectance of a surface to provide its reflectivity and estimated emissivity. The device is small and portable. It potentially provides either broadband (e.g., 3–12 $\mu$m) or spectral reflectance between near normal and grazing angles permitting pass-fail assessment of surface quality in the field.

Before describing the device, first we will discuss the significance of the measurements that the device allows us to make.

Both emission and reflection information are used to determine aircraft signature in conjunction with assumptions regarding the vehicle mission, flight environment, and speed. Requirements to measure reflectance vary from the relatively simple to the complex depending on the surface materials and the vehicle specification. Integrating spheres are commonly used with small samples to measure total and diffuse directional hemispherical reflectances. Bi-directional reflectance measurements can reveal specular lobe widths and other more detailed information but normally they require small samples and are very time consuming. These standard methods are not well suited for manufacturing quality control maintenance inspection or post-repair inspection. For NDE applications, a much simpler, cost-effective method is needed.

Directional emissivity $\epsilon(\lambda,\theta,\phi)$ is calculated from directional hemispherical reflectance $\rho(\lambda,\theta,\phi)$ as $\epsilon(\lambda,\theta,\phi)=1-\rho(\lambda,\theta,\phi)$. Directional hemispherical reflectance is typically measured using one of three methods:

(1) Illuminating at a specific angle of interest ($\theta,\phi$) and detecting hemispherically, typically by using an integrating sphere. Most total hemispherical reflectance measurements are made in this manner using angles of incidence near normal. Care must be taken in these measurements when measuring at incident angles of greater than 50°. If the sample surface is placed at the center of the sphere, it is impossible to measure an extended surface. If the material to be measured is placed on the integrating sphere wall, extended surfaces can be measured, however, the angle of incidence is limited because of the difficulty in placing the source at near grazing incidence without illuminating the sphere wall directly or without bumping the source into the surface. (2) Illuminating hemispherically and collecting radiation spectrally or band-averaged at the specific angle of interest for emission ($\theta,\phi$). An example of this type of system has been built by Surface Optics Corporation using a blackbody source at one focus of an ellipse and the sample at the other focus. The detector is moved between 10° and 80° off normal. This type of measurement provides an integrated directional reflectance, however, all information is lost relating to the angular distribution of the reflected radiation. (3) Integrating the bidirectional scatter measured over the hemisphere for a particular incident angle ($\theta,\phi$). This time consuming measurement and numerical integration produces a total hemispherical reflectance that includes the summation of many sources of error resulting in inaccurate data and conclusions.

None of these methods are known to be commercially available as handheld or portable devices in the infrared, except for the Surface Optics device mentioned earlier. Small hand-held reflectance devices for NDE are fairly common in the visible range and are used for measuring color or contamination. For example, Toomay Mathis provides small hand-held scatterometers which detect the bidirectional scatter at particular incident and detection angles. Bidirectional scatter measurements have limited value for evaluating signature related performance because there is no measurement or integration of the total reflected energy, only specific (and limited) information about the directional scatter.

Existing devices and measurement methods fall short of the need for NDE because they are not typically designed for measurements in the IR at the angles of interest, nor are they designed for NDE use (measurement times are too long), or the optical design does not permit viewing of an extended surface (limitations on sample size and curvature). In addition, no existing system will provide both directional scatter information (important for reflected contributions to the IR signature) and a total hemispherically integrated reflectance (important for calculating the emitted contribution to the signature).

In contrast to previous approaches, our reflectometer provides: (1) the ability to measure at incident angles of up to 85° or greater off normal, and (2) the ability to determine both an integrated total hemispherical reflectance with greater throughput than measurements using integrating spheres and an image of the scattered intensity over a hemisphere (some of our designs under consideration require an internal or external rotation of 180° to collect full hemispherical information for non-isotropic samples).

Our original device 100 for measuring the hemispherical reflectance formed a digital "image" of the angular distribution of the specularly and diffusely reflected radiation. The reflectometer illustrated in FIG. 5 uses the imaging properties of an ellipsoidal reflector 10. Light diverging from one focus 12 of the ellipse was specularly reflected and converged towards the second focus 14, but was redirected (in the embodiments of U.S. Pat. No. 5,637,873), by a secondary mirror 16. The major axis 18 which passed through the foci 12 & 14, was tilted relative to the sample surface to facilitate the collection of grazing-rays.

For an isotropic surface, for which all azimuthal orientations are equivalent, e.g. typical paints, it is sufficient to collect only half of the diverging rays if the symmetry of the problem is exploited. Illuminating the sample at the lower focus 12, the incident light generally an IR beam, must travel in a plane which passes through the lower focus and is perpendicular to both the sample surface and the plane of the figure. If the surface is anisotropic, complete hemispherical reflectance data can be obtained by making an additional measurement in which the beam orientation remains fixed relative to the sample surface but the instrument azimuth angle is rotated by 180°.

Figure 5:
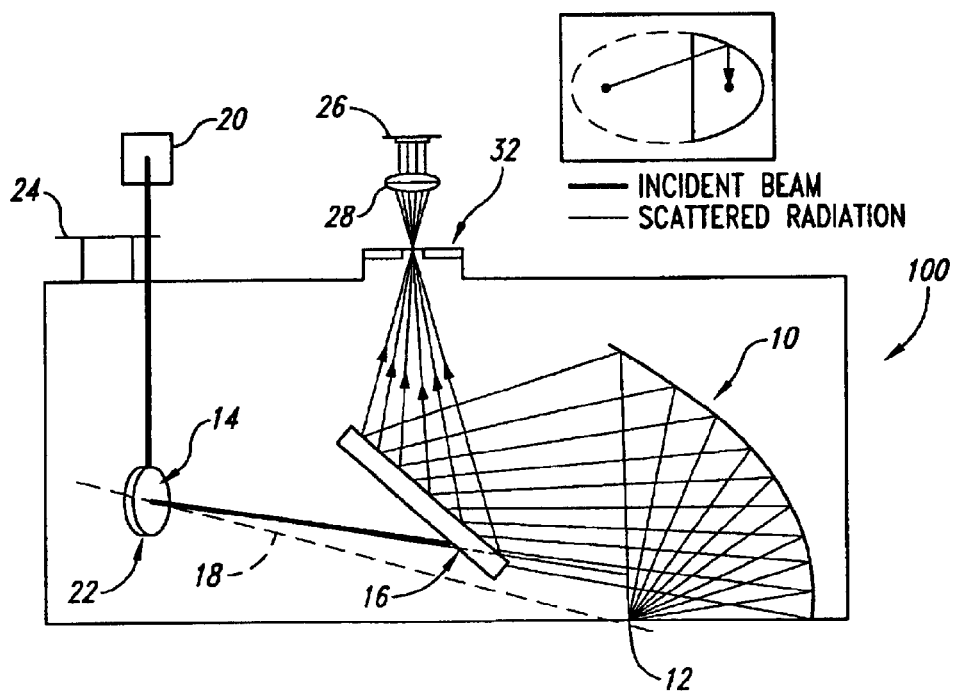
FIG. 5 is a schematic side elevation of another embodiment of a reflectometer.

The illumination scheme shown in FIG. 5 also utilizes the properties of the ellipsoid. A source 20, such as a blackbody, glow bar, or lamp is collimated to form a beam which is directed onto a mirror 22 located at the upper focus 14. The beam passes through a hole in the secondary mirror 16.and strikes the ellipsoidal reflector 10 which relays the beam to the lower focus 12 on the sample. With a gimbal mirror 22 which pivots on the upper focus 14 and an appropriate slot in the secondary mirror, the angle of incidence can be varied from normal to near grazing (>80°). A second slot or hole is needed to allow fixed illumination when the device is turned 180° for measuring non-isotropic surfaces. This design would probably also entail a translation of the secondary mirror to shift the unused hole to avoid losing the specular reflection of the beam.

One way to obtain hemispherical reflectance data is to allow the reflected rays to converge onto a large-area single-element detector. In the absence of the illuminating beam, the detector signal is proportional to the sum of the self-emitted and reflected radiation from the sample surface. If the measuring device is in thermal equilibrium with the sample, the total energy leaving the sample surface would equal that of a blackbody at the same temperature. When the illuminating beam is turned on, the change in detector signal is attributable to the specular and diffuse reflections of interest. In practice, this measurement will require chopping of the beam with a suitable beam chopper 24 and subtraction of the two detector signal levels to determine the desired reflectance.

The single detector approach provides a simple integrated number but ignores valuable information related to the details of the angular distribution of the reflected light. Such information can readily be obtained in the form of an image by using an IR focal plane array 26, or a scanning type imager. If the illuminating beam at the lower focus was of negligible extent, an image of the angular distribution is formed simply by displacing the detector plane in front or in back of the image focus. For an illumination spot of finite extent and an array of reasonable size, an image formed in this manner would have poor angular resolution. By using an appropriate lens 28, we can observe the far-field distribution pattern in the detector plane. As with the single detector, we use beam chopping and image subtraction to obtain the desired distribution. The cold aperture 32 is maintained at a low temperature with liquid nitrogen or another suitable cooling system to reduce emitted IR radiation impinging on the array.

While the energy distribution in these images will vary with sample material and angle of incidence, the grid 30 representing the mapping of angle space onto a 2-D plane will remain fixed. An optical raytrace code was used to determine the shape of this grid and it is shown in FIG. 6. The particular geometry corresponds to a focus separation of 3 inches and the upper focus 1 inch higher than the lower focus. The calculation assumes that the reflector surface extends well beyond the half hemisphere of interest. The grid lines are marked according to elevation angle and azimuth angle. For typical arrays and imagers, the output digital or video image is inverted and flipped left-to-right leading to a image that resembles the view from the inside of a globe.

A single number for the half-hemispherical reflectance can be obtained by adding up the intensity that falls within the +90° and −90° azimuth and the 0° to 90° elevation contours. Since typical arrays and imagers provide standard video outputs, there are many available choices of computer hardware and software to support the video image subtraction and processing. If desired, computer processing can remap the grid 30 to a more convenient shape, compute statistics describing the reflection or automatically compare the measured distribution with a stored ideal distribution to determine whether it is within allowed tolerance. With computer control over data acquisition and any moving parts in the device, we can make a rapid assessment of the bidirectional reflectance for incidence angles between normal and grazing. If reference samples are available, we make direct comparisons between coatings to negate any concerns about calibration drift. Also, we can use calibration samples such as diffuse and specular gold to verify proper operation of the measurement system.

The specific configuration shown in FIG. 5 is only one of many alternate designs for a reflectometer able to provide angle-space imaging of the directional scatter. The device in FIG. 5 uses a reflector and/or lens system to collect the light from a large solid angle and subsequently images the far field distribution pattern. Other reflector and illumination geometries or the use of lenses may also be suitable depending upon need and the desired level of sophistication.

Figure 8A:
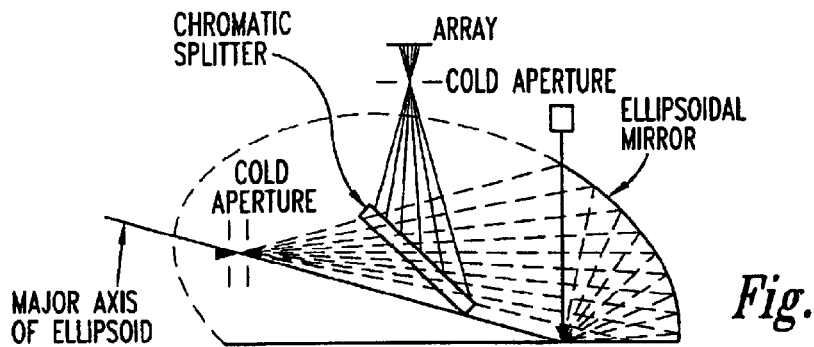
FIGS. 8A, 8B, 9A & 9B are variations, in plan view and side elevation, of the reflectometer of FIG. 5.
Figure 8B:
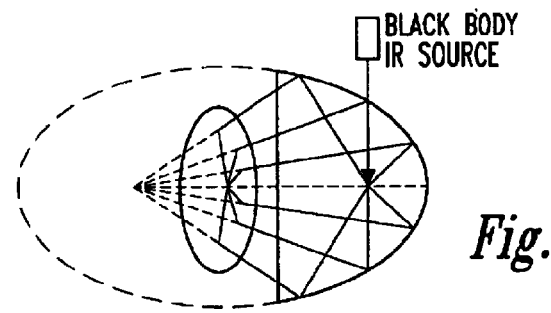

The alternate designs may be better for NDE applications. In particular, the concepts shown in FIGS. 1 and 8 provide full hemispherical coverage without moving parts.

The device in FIG. 5 is based on a truncated ellipsoidal reflector (cut off at both ends) and a series of lenses. One end of the reflector sits on the surface. The illumination beam enters through the side wall. Reflected radiation is separated (by the combined effects of the reflector and lens) into two distinct areas at the angular "image" plane: (1) radiation which is scattered from the sample at angles between 90° and 15° is reflected off the wall of the ellipsoidal reflector; these rays pass through the lens with limited change in direction; and (2) radiation scattered from the surface directly onto the lens is focused by the lens toward a focal point beyond the angular "image" plane.

The angular "image" in this plane, is shown as a doughnut-shaped section (reflections into angles between 15° and 90° in elevation (relative to the surface normal)) and a center section (reflections into angles between 0° and 15° in elevation).

From the angular "image" plane, the radiation is collected by a lens which has two sections, a positive (convex) lens and a negative (concave) lens. We can make this lens by cutting a hole in the convex lens and mounting the concave lens 412 in the center or we could use a special optic lens. Radiation emerges parallel from this lens, and is reduced by a series of two lenses (Galilean telescope) to fit on a small detector array.

Figure 9A:
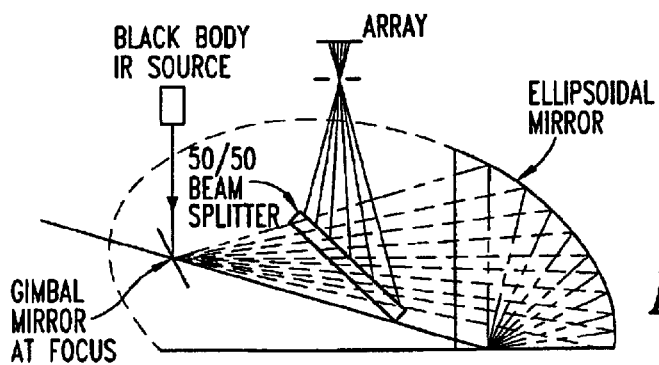
Figure 9B:
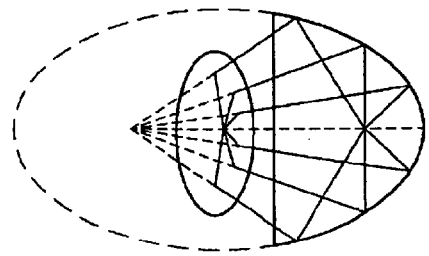
Figure 10A:
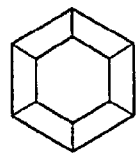
FIGS. 10A & 10B illustrate a variation using 7 lenses and 7 arrays.
Figure 10B:
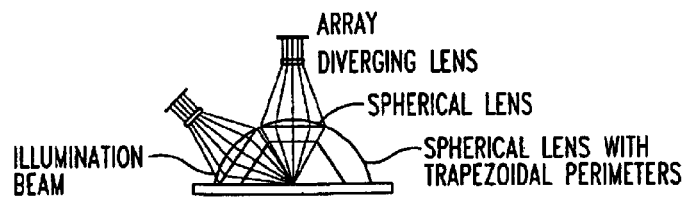
Figure 11:
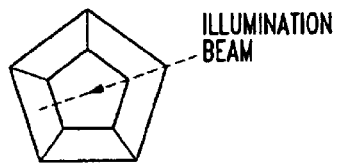
FIG. 11 illustrates another variation using 6 lenses and 6 arrays.
Figure 12A:
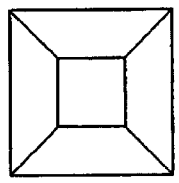
FIGS. 12A & 12B illustrate a variation using 5 lenses and 5 arrays.
Figure 12B:
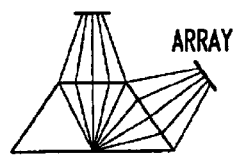

FIGS. 8 & 9 illustrate variations of the reflectometer design of FIG. 5. In FIG. 8 the incident light beam is injected through the ellipsoid wall and the detector array is included just beyond the upper focus of the ellipsoid. The device in FIG. 9 uses a 50/50 beam splitter in place of the secondary mirror to allow the incident beam to pass through the beam splitter at any desired angle withoutthe need for holes or slots.

Figure 13A:
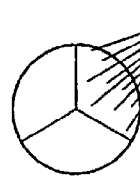
FIGS. 13A & 13B illustrate a variation using refraction of the scattered radiation by an array of three aspheric (or specially shaped) lenses.
Figure 13B:
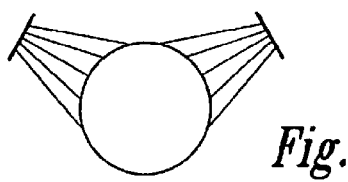
Figure 14A:
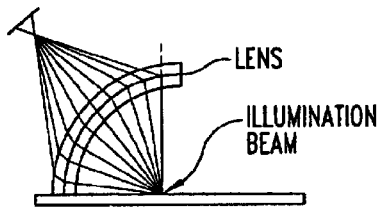
FIGS. 14A & 14B illustrate a variation using a single rotating lens to obtain full hemispherical coverage.
Figure 14B:
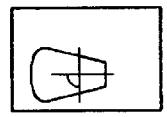

The concepts illustrated in FIGS. 10–13 are based on the refraction of the scattered radiation by a shaped lens array with as few as three lenses (FIG. 13). In these concepts, the lenses cover the hemisphere and each lens focuses the radiation from the sample onto an array set slightly away from the lens focus. Each of these lens systems could be fixed or reduced in the number of lenses and rotated. The reflectometer design illustrated in FIG. 14 may be the lowest cost, using only a single lens and array. In this concept the lens rotates about the vertical axis to provide full hemispherical coverage.

Figure 2:
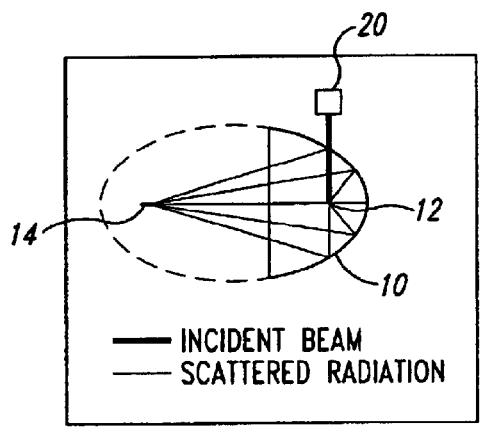
FIG. 2 is a top plan view of the reflectometer of FIG. 1.
Figure 3:
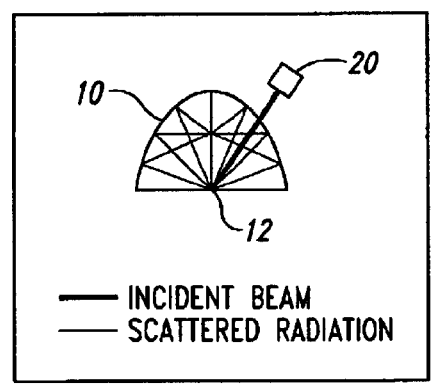
FIG. 3 is an end view looking at the ellipsoidal mirror of FIG. 1.
Figure 4:
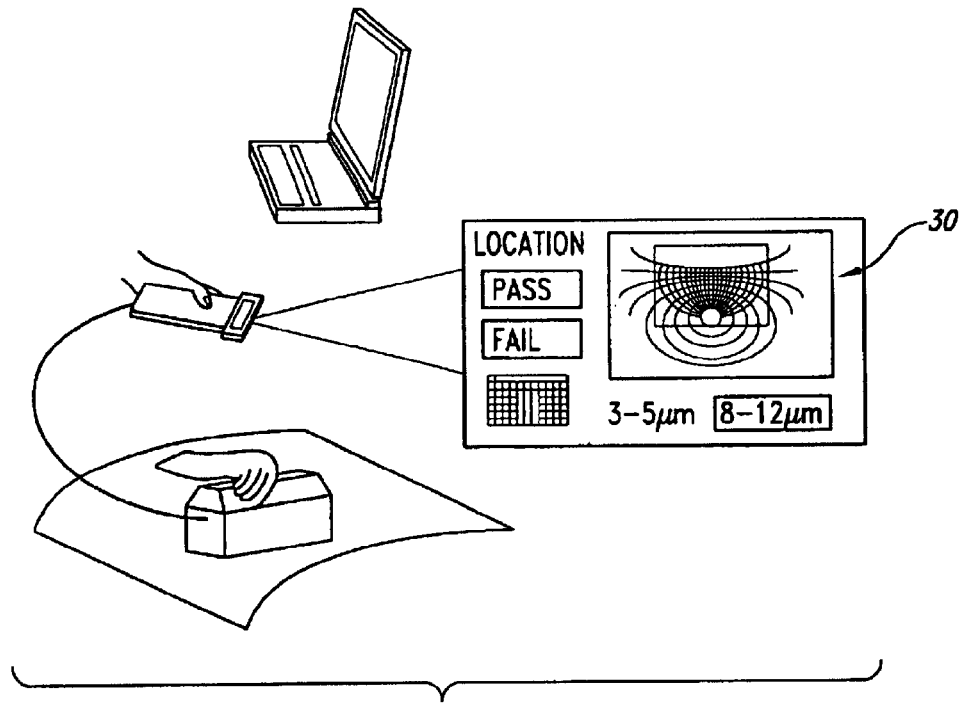
FIG. 4 is a schematic of a second embodiment of a directional reflectometer including an enlarged illustration of the screen display of a portable computer.

FIG. 1-3 show a preferred embodiment of our reflectometer that eliminates the cold aperture, gimbal mirror, and secondary mirror from the design shown in FIG. 5. The cold aperture is an option for an IR reflectometer. A cold aperture reduces background thermal contribution associated with the signal to permit higher resolution and discrimination. Eliminating the gimbal mirror 22 and secondary mirror 16 simplifies the design. As shown in FIG. 1, light within the frequency bandwidth of interest reflects from a surface at the lower focus of an ellipsoidal mirror. The reflection is directed toward an upper focus by the mirror where the light is collected with, an array detector and analyzed, as in the other embodiments.

While described primarily with reference to IR radiation, the concepts apply to other frequencies, especially the visible and UV, but even to microwave frequencies.

The directional reflectometer of the present invention is a compact system for measuring emissivity/reflectivity of coatings applied to laboratory coupons or to large objects which are not amenable to testing in the laboratory. The intended role is for quality assurance during manufacturing and in field service to verify that coatings are performing properly. The invention also enables a significant advancement in the laboratory measurement of surfaces because it provides a rapid and intuitive means of understanding the directionality of measured surfaces. We use reflective and refractive optics to form an "image" of the angular distribution of light reflecting from the surface of interest. Our concept allows virtually all of the IR light leaving a surface to be collected onto a single imaging array or possibly non-imaging detector.

The reflectometer is a small, traveling, broadband IR (3–12 μm) device or a UV, visible, and near IR (0.3–3 μm) device which is attached to a computer. The (computer analyzes the data collected at the imaging array and presents it in several formats, most notably a "pass-fail." In this device (1) reflection is measured at incident and reflected angles between near-normal and grazing (up to 88° from normal), (2) an angle-space "image" is formed of the scattered radiation, providing full directional reflectance information at a glance, and (3) the rapid response of this type of system allows data to be collected continuously as the device is moved across a surface. The angle-space "image" contains enough information to assess both standard and special surfaces or coatings and can be integrated to determine total hemispherical reflectance. Personal or laptop computer-based analysis permits rapid determination of pass-fail responses.

Our device for measuring the hemispherical reflectance forms a video "image" of the angular distribution of the specularly and diffusely reflected radiation. Our baseline design concept uses the imaging properties of an ellipsoidal reflector. Light diverging from one focus of the ellipse is specularly reflected and converges towards the second focus, but is redirected by a secondary mirror. In our configuration, the major axis which passes through the foci, is tilted relative to the sample surface to facilitate the collection of grazing rays.

The device functions as a light-gathering system which is a combination of an ellipsoid and lens system which gathers 2 distinct classes of light rays: rays reflecting from the surface and then off the ellipsoid mirror, and rays reflecting directly from the surface to be measured forming an annular ring pattern in the plane of a "bifocal" lens, including:

(a) an ellipsoidal mirror with two ends cut-off, one end is cut so that the surface to Ie measured is perpendicular to the major axis of the ellipsoid, and the surface passes through one of the ellipsoid foci;

(b) a simple or compound lens which is centered at the second ellipsoid focus and is sized large enough to collect those rays which do not interact with the ellipsoidal mirror;

(c) formation of an angular image plane;

(d) rays arriving at the angular image plane are of two classes:

(i) rays reflecting directly from the measured surface and forming the central core of the image, not interacting with the ellipsoidal mirror, and (ii) those rays reflecting off of the measured surface and then off of the ellipsoidal mirror which fill the annular ring of the image;

(e) a special "bifocal" lens or lens system placed at the image plane which is diverging to the core rays and converging to the rays in the annular ring, so as to make all rays exiting the angular image plane very nearly parallel.

(f) a reducing telescope to match the rays exiting the angular image plane to the selected sensor array or other imager or a single detector; and (g) the light beam can illuminate the surface to be measured over a wide range of angle, including near grazing angles.

While we have described preferred embodiments, those skilled in the art will readily recognize alterations, variations, and modifications which might be made without departing from the inventive concept. Therefore, interpret the claims liberally with the support of the full range of equivalents known to those of ordinary skill based upon this description. The examples illustrate the invention and not intended to limit it. Accordingly, limit the claims only as necessary in view of the pertinent prior art.

We claim:

1. A directional reflectometer, comprising:

(a) a source of radiation in a frequency range of interest for directing the radiation to a reflective test surface at incident angles between normal and grazing, up to about 88° from the normal;

(b) an ellipsoidal reflector, having an upper and lower focus, for receiving reflected radiation from the reflective test surface positioned at the lower focus;

(c) a detector positioned for receiving the reflected radiation from the ellipsoidal reflector that the ellipsoidal reflector reflects toward the upper focus and for displaying a signal representative of the angle-space distribution of the reflected radiation; and (d) optionally, computing means electronically connected with the detector for analyzing the reflected radiation, the computing means receiving the angle-space distribution signal from the detector.

2. The reflectometer of claim 1 further comprising a beam chopper associated with the source for determining the surface reflectance by a difference method.

3. The reflectometer of claim 1 wherein the detector includes at least one lens or mirror for focusing reflected radiation.

4. The reflectometer of claim 1 wherein the computing means includes a microprocessor and display, the display displaying the signal in a preselected format.

5. The directional reflectometer of claim 1 wherein the detector is an imaging detector for displaying the angle-space distribution signal as an image.

6. A method for measuring the reflectance of a surface, comprising the steps of:
   (a) illuminating the surface with radiation focused at the lower focus of an ellipsoidal mirror to produce a reflection at incident angles between normal and grazing, up to about 88° from the normal;
   (b) directing the reflection from the surface collected at the upper focus of the mirror to a detector, and
   (c) analyzing the reflection in the detector to determine the reflectance.

7. The method of claim 6 wherein analyzing involves creating an image representative of the reflection, the method further comprising the step of displaying the image on a display.

8. The method of claim 6 further comprising the step of signaling if the reflectance satisfies a criterion.

9. The method of claim 6 wherein the detector forms an image of the reflection.

10. A method for forming a resolved image of the angular distribution of light reflected, scattered, or emitted from a surface, comprising the steps of:
   (a) illuminating a region of a surface at incident angles between normal and grazing, up to about 88° from the normal;
   (b) collecting a large angular range of light rays leaving the illuminated region with a lens or mirror causing the rays to reconverge toward a focus; and
   (c) either (i) intercepting the rays near the focus with an angle scanning imager or (ii) using a collimating optic beyond the focus to produce approximately parallel rays which are intercepted by an imaging ray.

* * * * *